(12) United States Patent
Zaveri

(10) Patent No.: US 6,767,891 B2
(45) Date of Patent: Jul. 27, 2004

(54) PEPTIDES WITH WOUND HEALING ACTIVITY

(76) Inventor: Chanda Zaveri, 6740 Los Verdes Dr. #8, Rancho Palos Verdes, CA (US) 90275

( * ) Notice: Subject to any disclaimer, the term of this patent is extended or adjusted under 35 U.S.C. 154(b) by 21 days.

(21) Appl. No.: 09/879,666

(22) Filed: Jun. 12, 2001

(65) Prior Publication Data

US 2002/0082196 A1 Jun. 27, 2002

Related U.S. Application Data

(60) Provisional application No. 60/211,859, filed on Jun. 14, 2000.

(51) Int. Cl.$^7$ .......................... A61K 35/16; C07K 14/00
(52) U.S. Cl. ............................... 514/2; 514/8; 530/300; 530/324; 530/350; 530/351
(58) Field of Search ................................. 530/324, 300, 530/350, 351; 424/85.1; 514/2, 8, 12

(56) References Cited

U.S. PATENT DOCUMENTS 6,287,606 B1 * 9/2001 Bockman et al.
6,319,907 B1 * 11/2001 Ferguson
6,331,409 B1 * 12/2001 Livant

* cited by examiner

*Primary Examiner*—Elizabeth Kemmerer
(74) *Attorney, Agent, or Firm*—Catalyst Law Group; Michael B. Farber, Esq.

(57) ABSTRACT

A number of peptides of from 28 to 44 amino acids, including therein a sequence of L-K-E-K-K (SEQ ID NO: 1), have a physiological activity that can be wound healing activity, immunostimulant activity, or growth factor activity. The peptides can be linear or circular, and, if linear, its amino terminus can be optionally acetylated. The invention also includes nucleic acids encoding these peptides, vectors incorporating these nucleic acid sequences, and host cells transfected with these vectors, as well as methods for producing these peptides by culturing these host cells and purifying the peptides. The invention further includes pharmaceutical compositions and methods for using these peptides.

3 Claims, 14 Drawing Sheets

(8 of 14 Drawing Sheet(s) Filed in Color)

FIG. 7
FIG. 8
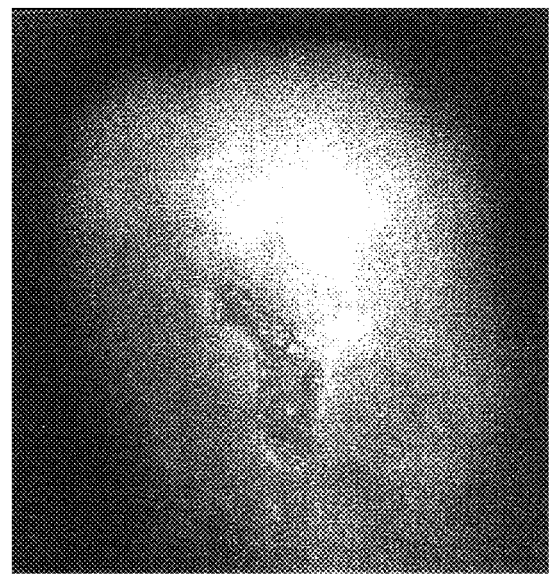

FIG. 9
FIG. 10

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptides with Physiological Activity

<400> SEQUENCE: 1

Leu Lys Glu Lys Lys
 1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Leu Lys Glu Lys Lys Glu
 1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptides with Physiological Activity

<400> SEQUENCE: 3

Leu Lys Glu Lys Lys Glu Val Val Glu
 1               5

<210> SEQ ID NO 4
<211> LENGTH: 28
<212> TYPE: PRT
<213> ORGANISM: Artificial Sequence
<220> FEATURE:
<223> OTHER INFORMATION: Synthetic Peptides with Physiological Activity
<221> NAME/KEY: ACETYLATION
<222> LOCATION: (1)...(0)
<223> OTHER INFORMATION: Acetylated amino terminal residue

<400> SEQUENCE: 4

Ser Asp Ala Ala Val Asp Thr Ser Ser Glu Ile Thr Thr Lys Asp Leu
```

```
                    1               5                   10                  15
Lys Asp Lys Lys Glu Val Val Glu Glu Ala Glu Asn
                    20                  25

<210> SEQ ID NO 5
<211> LENGTH: 35
<212> TYPE: PRT
<213> ORGANISM: Artificial Sequence
<220> FEATURE:
<223> OTHER INFORMATION: Synthetic Peptides with Physiological Activity

<400> SEQUENCE: 5

Lys Leu Lys Lys Thr Glu Thr Glu Gln Lys Asn Pro Leu Glu Val Leu
  1               5                   10                  15

Lys Glu Lys Lys Glu Val Val Glu Leu Lys Glu Lys Lys Val Val Ile
                    20                  25                  30

Glu Asn Pro
        35

<210> SEQ ID NO 6
<211> LENGTH: 38
<212> TYPE: PRT
<213> ORGANISM: Artificial Sequence
<220> FEATURE:
<223> OTHER INFORMATION: Synthetic Peptides with Physiological Activity
<221> NAME/KEY: ACETYLATION
<222> LOCATION: (1)...(0)
<223> OTHER INFORMATION: Amino terminal residue acetylated

<400> SEQUENCE: 6

Ala Asp Lys Pro Met Gly Glu Ile Ala Ser Phe Asp Lys Ala Gly Leu
  1               5                   10                  15

Lys Glu Lys Lys Glu Thr Leu Pro Thr Lys Glu Thr Ile Glu Glu Glu
                    20                  25                  30

Lys Arg Ser Glu Ile Ser
        35

<210> SEQ ID NO 7
<211> LENGTH: 44
<212> TYPE: PRT
<213> ORGANISM: Artificial Sequence
<220> FEATURE:
<223> OTHER INFORMATION: Synthetic Peptides with Physiological Activity
<221> NAME/KEY: ACETYLATION
<222> LOCATION: (1)...(0)
<223> OTHER INFORMATION: Amino terminal residue acetylated

<400> SEQUENCE: 7

Ala Asn Lys Gly Gln Ala Pro Gly Glu Ala Met Lys Pro Ser Phe Leu
  1               5                   10                  15

Lys Glu Lys Lys Glu Val Val Glu Arg Ser Lys Glu Glu Gly Pro
                    20                  25                  30

Ala Lys Met Asn Leu Val Ile Glu Met Pro Lys Asp
        35                  40

<210> SEQ ID NO 8
<211> LENGTH: 43
<212> TYPE: PRT
<213> ORGANISM: Artificial Sequence
<220> FEATURE:
<223> OTHER INFORMATION: Synthetic Peptides with Physiological Activity

<400> SEQUENCE: 8

Lys Lys Leu Lys Lys Glu Glu Asn Pro Leu Glu Leu Lys Glu Lys Leu
```

```
                        -continued
1            5              10              15
Lys Lys Glu Lys Lys Asn Pro Leu Pro Ser Lys Glu Glu Glu Lys Ala
            20              25              30

Ser Pro Asp Lys Ile Glu Thr Pro Asp Met Ser
        35              40
```

PEPTIDES WITH WOUND HEALING ACTIVITY

CROSS-REFERENCES

This application claims priority from Provisional Application Serial No. 60/211,859 by Chanda Zaveri, filed Jun. 14, 2000, entitled "Peptides with Physiological Activity," which is incorporated herein in its entirety by this reference.

BACKGROUND OF THE INVENTION

This invention is directed to peptides with various physiological activities, particularly wound healing.

Wound healing is a complex biological process that differs according to the wound type: acute or chronic. The principal elements of wound repair are the immediate events of hemostatis and stimulus for inflammation, then inflammation and cell proliferation and migration, then followed by molecular synthesis, collagen polymerization and cross-linking, remodeling, and wound contraction. Inflammation is characterized by vasodilation, increased vascular permeability, leukocyte infiltration, bacterial killing, and macrophage-based stimulation of cellular proliferation and protein synthesis.

In cell proliferation and migration, fibroblasts appear within 2–3 days and dominate wound cell population during the first week. For the initial 2–3 days, their activity is confined to fibroblast replication and migration. At days 4–5, fibroblasts begin to synthesize and secrete extracellular collagen. Fibroblasts produce GAG and collagen.

Angiogenesis is essential to wound repair and scar formation. Capillary proliferation is required to support fibroblast migration into wound and fibroblast metabolic requirements. In the absence of angiogenesis, such as in ischemic ulcers or arteriosclerosis obliterans, fibroblast migration arrests and wound healing fails to proceed.

Angiogenesis has the stages of cell attachment, basement membrane degradation and migration, proliferation, and differentiation, and is associated with epithelial cell migration.

Molecular synthesis includes collagen synthesis and proteoglycan synthesis. Collagen synthesis begins with the intracellular phase of monomer synthesis. Secretion into the extracellular space then occurs, followed by polymerization into collagen fibers and cross-linking to increase tensile strength.

Remodeling typically begins 3 weeks after injury. Equilibrium between collagen synthesis and degradation is achieved. Wound remodeling begins and will continue for 2 years. There is a progressive increase in tensile strength as Collagen III is replaced by Collagen I. Epithelialization is the hallmark of successful wound repair and occurs in four phases: mobilization, migration, mitosis, and cellular differentiation.

Granulation tissue contains numerous capillaries and has a support matrix rich in fibroblasts, inflammatory cells, endothelial cells, myofibroblasts, and periocytes. If vascular endothelial growth factor (VEGF) is removed, there is an absence of granulation tissue, and wound angiogenesis and the wound healing process cease.

In chronic wound healing, there is typically an absence of epithelial migration, excessive granulation tissue, and fibrosis, with scarring and impaired function possibly being present.

Although many advances have been made in the understanding of wound healing, the healing of wounds still presents a considerable challenge to the clinician. This is particularly true in patients who are diabetic, who have impaired circulation of the skin, or who are susceptible to infection, such as the result of being in an immunocompromised condition. Additionally, when such wounds do heal, they frequently heal with cosmetically undesirable consequences such as scars or discoloration.

Accordingly, there is a need for an improved method of wound healing that is particularly suitable for application in patients with diabetes, who have poor circulation in the skin, or who are immunocompromised. There is a further need for treatments and methods that can reduce or eliminate the consequences that can occur from wound healing, such as scars and discoloration. There is an additional need for factors that are well-tolerated and can be used with other treatments in such patients.

SUMMARY

One aspect of the present invention is a substantially purified peptide having a physiological activity, the peptide comprising a sequence from 28 to 44 amino acids, including therein a sequence of L-K-E-K-K (SEQ ID NO: 1), the peptide having a physiological activity selected from the group consisting of wound healing activity, immunostimulant activity, and growth factor activity, wherein the peptide is in linear or cyclic form, and wherein the peptide is in linear form, the amino terminus is optionally acetylated. The sequence within this peptide can be L-K-E-K-K-E (SEQ ID NO:2) or L-K-E-K-K-E-V-V-E (SEQ ID NO: 3).

The invention includes the following peptides:

(1) a substantially purified peptide having wound healing activity, the peptide comprising a sequence of 28 amino acids, that is: Ac-S-D-A-A-V-D-T-S-S-E-I-T-T-K-D-L-K-E-K-K-E-V-V-E-E-A-E-N (SEQ ID NO: 4), where "Ac" indicates that the amino terminus is acetylated, the peptide being linear;

(2) a substantially purified peptide having wound healing activity, the peptide comprising a sequence of 35 amino acids, that is: K-L-K-K-T-E-T-E-Q-K-N-P-L-E-V-L-K-E-K-K-E-V-V-E-L-K-E-K-K-V-V-I-E-N-P (SEQ ID NO: 5), the peptide being linear;

(3) a substantially purified peptide having immunostimulant activity, the peptide comprising a sequence of 38 amino acids, that is: Ac-A-D-K-P-M-G-E-L-A-S-F-D-K-A-G-L-K-E-K-K-E-T-L-P-T-K-E-T-I-E-E-E-K-R-S-E-I-S (SEQ ID NO: 6), the peptide being linear;

(4) a substantially purified peptide having wound healing activity, the peptide comprising a sequence of 44 amino acids, that is: Ac-A-N-K-G-Q-A-P-G-E-A-M-K-P-S—F-L-K-E-K-K-E-V-V-E-R-S-K-E-E-G-P-A-K-M-N-L-V-I-E-M-P-K-D (SEQ ID NO: 7), the peptide being linear; and (5) a substantially purified peptide having wound healing activity the peptide comprising a sequence of 44 amino acids, that is: K-K-L-K-K-E-E-N-P-L-E-L-K-E-K-L-K-E-K-K-N-P-L-P-S-K-E-E-K-A-S-P-F -D-K-J-T-E-T-P-D-M-S (SEQ ID NO: 8), the peptide being linear.

Another aspect of the present invention is an isolated nucleic acid molecule encoding a peptide of the present invention. Typically, this nucleic acid molecule is DNA.

Yet another aspect of the present invention is a vector comprising DNA according to the present invention operably linked to at least one control element that influences the expression of the DNA Still another aspect of the present invention is a host cell transfected with a vector according to the present invention such that the cell expresses the peptide encoded by the vector according to the present invention.

Another related aspect of the present invention is a method of producing a substantially purified peptide having a physiological activity comprising the steps of:

(1) culturing a host cell according to the present invention; and (2) isolating the peptide produced by the host cell to produce the substantially purified peptide.

Yet another aspect of the present invention is a pharmaceutical composition comprising:

(1) a peptide according to the present invention in a physiologically effective quantity; and (2) a pharmaceutically acceptable carrier.

A particularly preferred pharmaceutically acceptable carrier comprises water, Seamollient, a polymer selected from the group consisting of carboxymethylcellulose and hydroxyethylcellulose, and at least one preservative selected from the group consisting of methylparaben and propylparaben.

Still another aspect of the present invention is a method of use of a peptide according to the present invention for promoting wound healing, stimulating the immune system, or stimulating pituitary/hypothalamus activity in a mammal in need thereof comprising administering an effective quantity of a peptide according to the present invention having the appropriate activity to the mammal.

BRIEF DESCRIPTION OF THE DRAWINGS

This patent contains at least one drawing executed in color.

FIG. 7 is a photograph of the ulcer after additional treatment with $TB_4$, showing continued improvement;

FIG. 8 is a photograph of the ulcer after treatment with $TB_4$ had been temporarily suspended for one week;

FIG. 9 is a photograph of the ulcer after treatment with $TB_4$ had been restarted;

FIG. 10 is a photograph of the ulcer after further treatment;

DETAILED DESCRIPTION OF THE PREFERRED EMBODIMENTS

1. Peptides having Physiological Activity

A. General Description

Figure 1:
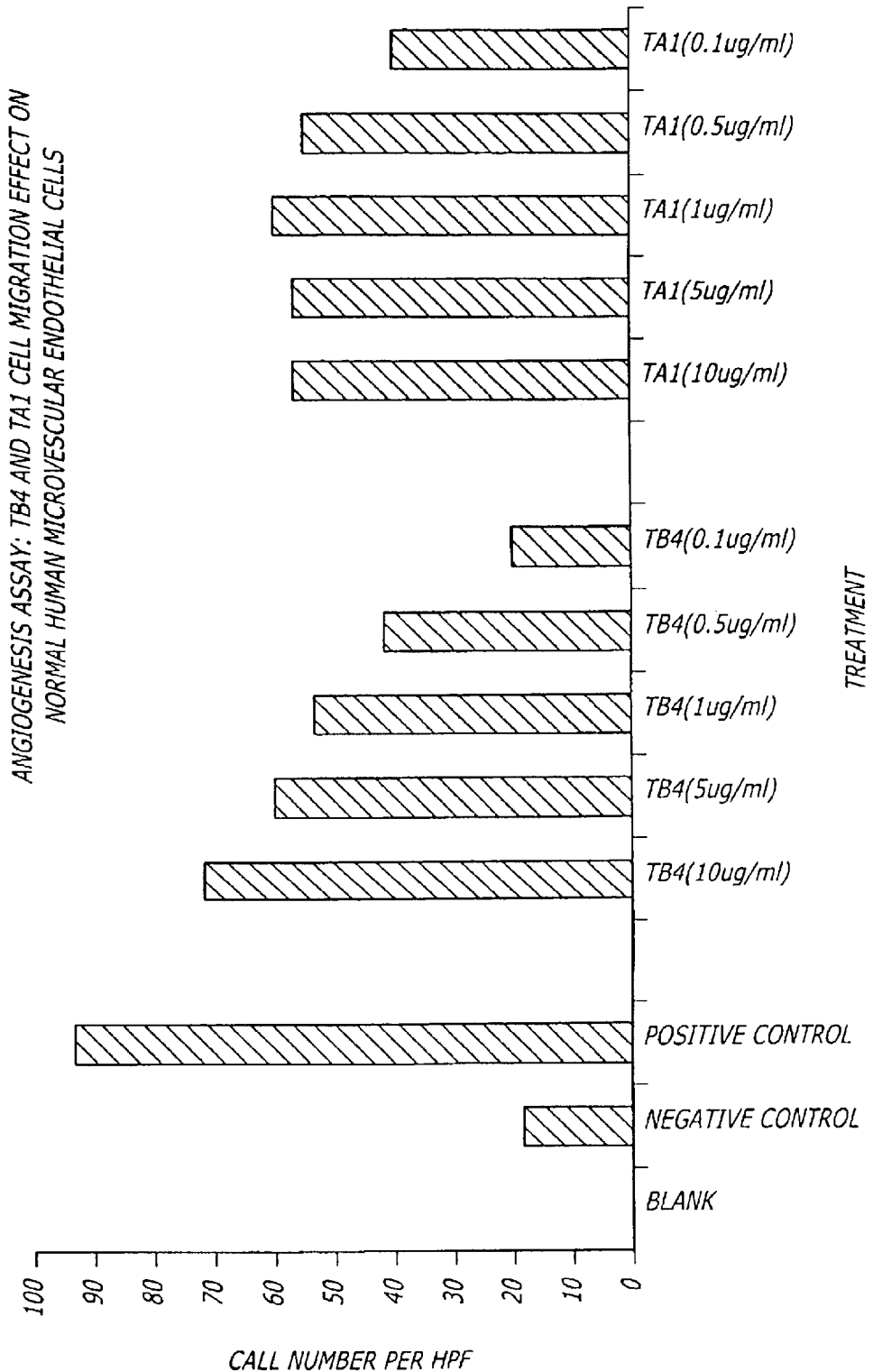
FIG. 1 is a graph showing the effects of the peptides $TB_4$ and $TA_1$ on endothelial cell migration in a Boyden chamber migration assay.

One aspect of the invention is substantially purified peptides having a physiological activity. The physiological activity can be one or more of wound healing activity, immunostimulant activity, and growth factor activity, particularly growth factor activity directed toward the pituitary or hypothalamus. Peptides according to the present invention typically have a spectrum of activities that includes wound healing activity and can include one or more of the other activities recited above. The peptide comprises a sequence of from 28 to 44 amino acids and includes therein a sequence of L-K-E-K-K (SEQ ID NO:1). This sequence can be extended so that it is L-K-E-K-K-E (SEQ ID NO:2) or L-K-E-K-K-E-V-V-E (SEQ ID NO:3). As indicated below with respect to the specific peptides that are aspects of this invention, this sequence is substantially invariant.

Peptides according to the present invention can be linear or circular. If the peptide is linear, the amino terminus is optionally acetylated.

In the context of this specification, the term "substantially purified" refers to a state of purity that is at least 50%, preferably at least 70%, more preferably at least 85%, and still more preferably at least 95%, and in which the peptide having physiological activity is present in the substantial absence of other peptides or proteins having physiological activity.

B. Specific Peptides of the Invention

1. Peptide $TA_1$

One of the peptides of the present invention is a 28-amino acid peptide having wound healing activity, designated $TA_1$.

The peptide has the sequence SEQ ID NO:1: Ac-S-D-A-A-V-D-T-S-S-E-I-T-T-K-D-L-K-E-K-K-E-V-V-E-E-A-E-N. In this peptide and other peptides of the present invention, the notation "Ac" at the amino terminus of the peptide indicates that the amino terminus is acetylated. Generally, this acetyl group can be cleaved without impairing the function of the peptide. This peptide is linear. This peptide has an acetylated amino terminus and has a molecular weight of 3071 Daltons. The isoelectric point of this peptide is 4.1, indicating a predominance of acidic amino acids. This peptide has wound healing activity and may be derived by cleavage of thymosin.

2. Peptide $TA_2$

Peptide $TA_2$ is a 35-amino-acid-peptide also having wound healing activity which has a sequence of SEQ ID NO:5: K-L-K-K-T-E-T-E-Q-K-N-P-L-E-V-L-K-E-K-K-E-V-V-E-L-K-E-K-K-V-V-I-E-N-P. This peptide is linear and has a free, unblocked amino terminus. This peptide incorporates the conserved sequence of L-K-E-K-K-E-V-V-E (SEQ ID NO:3)

3. Peptide $TA_3$

Another peptide that is an aspect of the present invention is a peptide designated $TA_3$. This is a peptide of 38 amino acids that has immunostimulant activity. This peptide has the sequence SEQ ID NO:6: Ac-A-D-K-P-M-G-E-I-A-S-F-D-K-A-G-L-K-E-K-K-E-T-L-P-T-K-E-T-I-E-E-E-K-R-S-E-I-S. This peptide is linear, and has an acetylated amino terminus. This peptide incorporates the conserved sequence of L-K-E-K-K-E (SEQ ID NO:2).

4. Peptide $TB_4$

Peptide $TB_4$ is a peptide of 44 amino acids having wound healing activity. This peptide has the sequence SEQ ID NO:7: Ac-A-N-K-G-Q-A-P-G-E-A-M-K-P-S-F-L-K-E-K-K-E-V-V-E-R-S-K-E-E-E-G-P-A-K-M-N-L-V-I-E-M-P-K-D. This peptide is linear. The amino terminus of this peptide is acetylated. This peptide contains the conserved sequence L-K-E-K-K-E-V-V-E (SEQ ID NO:3).

5. Peptide $TA_5$

Another aspect of the invention is a peptide designated TA5, which has 44 amino acids. This peptide has wound healing activity. This peptide has a sequence of 44 amino acids, which is SEQ ID NO: 8: K-K-L-K-K-E-E-N-P-L-E-L-K-E-K-L-K-E-K-K-N-P-L-P-S-K-E-E-E-K-A-S-P-F-D-K-I-T-E-T-P-D-M-S. This peptide is linear and has a free, unblocked amino terminus. This peptide includes the highly conserved region L-K-E-K-K (SEQ ID NO: 1).

In addition, peptides having conservative amino acid substitutions except in the highly conserved sequences of L-K-E-K-K (SEQ ID NO:1), L-K-E-K-K-E (SEQ ID NO:2), or L-K-E-K-K-E-V-V-E (SEQ ID NO:3) are within the scope of the present invention. It is a well-established principle of protein and peptide chemistry that certain amino acid substitutions, entitled "conservative" amino acid substitutions, can frequently be made in a protein or a peptide without altering either the conformation or the function of the protein or peptide. Such changes including substituting any of isoleucine (I), valine, and leucine (L) for any other of these amino acids; aspartic acid (D) for glutamic acid (E) and vice versa; glutamine (Q) for asparagine (N) and vice versa; and serine for threonine (T) and vice versa. The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine. Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Cysteine (C) can frequently be replaced by serine when cysteine's capacity to form disulfide bond is either undesirable or unneeded. Still other changes can be considered "conservative" in particular environments.

As indicated above, the peptides of the present invention can be either circular or linear. The specific peptides described above, however, are linear. Some of the peptides of the present invention have their amino termini blocked, typically by acetylation. However, these acetyl groups can be cleaved by hydrolysis without interfering with the function of the peptides.

II. Nucleic Acids Encoding the Peptides

Another aspect of the present invention is isolated nucleic acids encoding a peptide according to the present invention, particularly the peptides of SEQ ID NO:4, SEQ ID NO:5, SEQ ID NO:6, SEQ ID NO:7, and SEQ ID NO:8. As used herein, the term "nucleic acid" includes both DNA and RNA and both single-stranded and double-stranded forms; if double-stranded, DNA-RNA hybrids are also included. Recitation of a single-stranded nucleic acid sequence also includes its complement according to the generally accepted Watson-Crick rules for base pairing. Nucleic acids encoding these peptides can either be DNA or RNA; however, in many applications, DNA is preferred.

The term "isolated" is used herein to indicate that the nucleic acids are present in substantial isolation from nucleic acid molecules that do not encode a peptide according to the present invention. In the context of this specification, the term "isolated" refers to a state of purity that is at least 50%, preferably at least 70%, more preferably at least 85%, and still more preferably at least 95%.

However, nucleic acids according to the present invention can be incorporated into larger nucleic acid molecules such as vectors for transfection of appropriate host cells and production of a peptide according to the present invention, and the term "isolated" is not to be interpreted to preclude this incorporation into larger, genetically-engineered molecules not occurring in nature.

The sequence of the nucleic acids is chosen according to the conventional triplet genetic code to encode the amino acid sequence of the particular peptides. Because the genetic code, which specifies amino acids by triplet codons in the nucleic acid sequence, is degenerate, and many amino acids are specified by more than one codon, all possible alternatives of codons can be used. However, in some cases, the efficiency of transcription and/or translation of the nucleic acid sequences can be affected by the codon selection. In such cases, it is preferred to use codons that provide increased efficiency of transcription and/or translation of the nucleic acid sequences.

III. Vectors and Host Cells

Another aspect of the present invention is a vector comprising a DNA according to the present invention operably linked to at least one control element that influences the expression of the DNA. These control elements can be promoters, operators, enhancers, or other nucleic acid sequences that affect the expression of the DNA. The vector can be derived from either prokaryotic or eukaryotic sources. The vector can comprise sequences of chromosomal, non-chromosomal, or synthetic DNA sequences. Typically, these vectors include one or more cloning sites that contain restriction endonuclease sequences that are readily cleavable by specific restriction endonucleases. It is generally preferred that these restriction endonucleases yield cohesive or "sticky" ends for more efficient cloning in of the desired sequence. Some suitable prokaryotic cloning vectors include plasmids from *Escherichia coli*, such as colE1, pCR1, pBR322, pMB9, pUC, pKSM, or RP4. Prokaryotic vectors also include derivatives of bacteriophage DNA such as M13 and other filamentous single-stranded DNA phages. Other vectors, such as baculovirus vectors, can be used.

Examples of useful expression controlled sequences are the lac system, the trp system, the tac system, the trc system, major operator and promoter regions of bacteriophage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters of SV40 and other sequences known to control the expression of genes of prokaryotic or eukaryotic cells and their viruses or combinations thereof. Vectors useful in yeast are available. A suitable example is the $2\mu$ plasmid. Vectors for use in animal cells are also known. These vectors include derivatives of SV40, adenovirus, retrovirus-derived DNA sequences, and shuttle vectors derived from combinations of functional mammalian vectors, such as those described above, and functional plasmids and phage DNA.

Another suitable vector is the baculovirus vector.

In general, however, it is preferred to use a vector that is suitable for expression in *E. coli*.

Vectors are inserted into a host cell for expression. Typically, these vectors are inserted into a host cell by methods well-known in the art, such as transfection, transformation, electroporation, direct injection of the DNA, lipofection, and other well-understood methods. The method to be used can be chosen according to the host cells selected and the size and conformation of the DNA. Some useful expression host cells include well-known prokaryotic and eukaryotic cells. Some suitable prokaryotic hosts include, for example, *E. coli*, such as *E. coli* SG-936, *E. coli* HB101, *E. coli* W3110, *E. coli* •1776, *E coli* •2282, *E. coli* DHI, and *E. coli* MRCI. Other bacterial and fungal host cells could be used, such as Pseudomonas, Bacillus species, such as *Bacillus subtilis*, and Streptomyces. Other host cells that can be used are eukaryotic cells such as yeast and other fungi, insect cells, animal cells, such as COS cells and CHO cells, human cells, and plant cells in tissue culture.

IV. Methods of Preparation of Peptides

A. Solid-State Peptide Synthesis

Peptides according to the present invention can be synthesized by standard solid-state peptide synthesis methods, such as those described in M. Bodanszky, "Principles of Peptide Synthesis" (Springer-Verlag, Berlin, 2d ed., 1993). This involves synthesis on an insoluble polymer such as a styrene-divinylbenzene copolymer that is derivatized. The sequence of reactions used is standard.

B. Genetic Engineering

Peptides according to the present invention can be prepared by genetic engineering. In general, a method of producing a substantially purified peptide according to the present invention having a physiological activity comprises the steps of: (1) culturing a host cell transfected with a vector comprising DNA encoding the peptide operably linked to at least one control element that influences the expression of the DNA; and (2) isolating the peptide produced by the host cell to produce the substantially purified peptide.

Expression methods are described in, e.g., D. V. Goeddel, "Gene Expression Technology" (Academic Press, San Diego, 1991). In general, such methods are well known in the art.

Once expressed, the peptides of the present invention can be isolated by standard protein isolation techniques including ion-exchange chromatography on resins such as diethylaminoethylcellulose or carboxymethylcellulose, chromatography on size exclusion media (gel filtration), isoelectric focusing, chromatofocusing, and other standard methods, such as those described in R. K. Scopes, "Protein Purification: Principles and Practice" (3d Ed., Springer-Verlag, New York, 1994).

If polyclonal or monoclonal antibodies are prepared to these peptides, these antibodies can be used in affinity chromatography by standard methods such as those described in the above-identified Scopes book. Such methods for the preparation of polygonal antibodies or monoclonal antibodies are well known in the art and need not be described in further detail here. In general, polyclonal antibodies are produced by injecting the peptides of the present invention, with or without a suitable adjuvant such as Freund's complete adjuvant, into an antibody-producing mammal such as a rat, a rabbit, a sheep, or a goat. The peptide can be coupled to a carrier protein such as keyhole limpet hemocyanin. Once polyclonal antibodies are produced, cells producing such polyclonal antibodies can be fused with appropriate fusion partners by standard techniques to yield hybridomas producing monoclonal antibodies of defined specificity.

V. Methods of Use

Peptides according to the present invention can be administered by a number of routes. When used for wound healing, they are typically administered topically to the skin or other mucous membranes. However, when they are administered as immunostimulants or as growth factors to stimulate pituitary or hypothalamus function, they can be administered by other routes, such as intramuscularly, intravenously, intradermally, or by other routes. A preferred dose is 0.5 ml of 100 $\mu$g/ml solution of the peptide or a dose of 50 $\mu$g of the peptide.

The dosages to be administered can be determined by one of ordinary skill in the art depending on the clinical severity of the disease, the age and weight of the patient, the exposure of the patient to conditions that may affect the course of wound healing, the existence or nonexistence of underlying systemic problems such as diabetes, impaired circulation, and immunocompromised status, and other pharmacokinetic factors generally understood in the art, such as liver and kidney metabolism. The interrelationship of dosages for animals of various sizes and species and humans based on mg/m3 of surface area is described by E. J. Freireich et al., "Quantitative Comparison of Toxicity of Anticancer Agents in Mouse, Rat, Hamster, Dog, Monkey and Man," *Cancer Chemother. Rep.* 50: 219–244 (1966). Adjustments in the dosage regimen can be made to optimize the therapeutic response. Doses can be divided and administered on a daily basis or the dose can be reduced proportionally depending on the therapeutic situation.

Methods according to the present invention can be used to treat humans or socially or economically important animal species such as dogs, cats, horses, sheep, cows, goats, or pigs. Methods according to the present invention are not limited to use in humans.

The peptides of the present invention that promote wound healing are suitable for use in the following situations in which wound healing is required: (1) diabetic foot and leg ulcerations, including neuropathic ulcerations, decubitus lesions, and necrobiosis lipoidica diabeticorum; (2) vascular ulcerations, including venous stasis ulceration, arterial ulcerations, varicose vein ulcerations, post-thrombotic ulcerations, atrophie blanche ulcerations, congenital absence of veins/ulcerations, congenital or traumatic arteriovenous anastomosis, temporal arteritis, atherosclerosis, hypertension (Martorell's ulcerations), thrombosis, embolism, platelet agglutination, ankle blow-out syndrome, or hemangiomas; (3) decubitus ulcers or pressure source (e.g., with bed rest); (4) traumatic ulcerations, such as those caused by external injuries, burns, scalds, chemical injuries, post-surgical injuries, self-inflicted injuries, lesions at an injection site, neonatal or perinatal trauma, or sucking blisters; (5) infestations and bites, such as those caused by spiders, scorpions, snakes, or fly larvae (mydriasis); (6) cold injury, such as perniosis (erythrocyanosis frigida), or cryoglobulinemic ulcerations; (7) neoplastic ulceration, such as those caused by basal cell carcinomas, squamous cell carcinomas, malignant melanomas, lymphoma, leukemia, Kaposi's sarcoma, tumor erosion, midline lethal granuloma, or Wegener's granulomatosis; (8) blood diseases with ulcerations, such as polycythemia, spherocytosis, or sickle cell anemia; (9) skin diseases with ulcerations, such as tinea, psoriasis, pemphigoid, pemphigus, neurotic excoriations, trichotillomania, erosive lichen planus, or chronic bullous dermatosis of childhood; (10) metabolic disease ulcerations, such as those associated with diabetes mellitus or gout (hyperuricemia); (11) neuropathic ulcerations, such as those associated with diabetes mellitus, tabes dorsalis, or syringomyelia; (12) ischemic ulcerations, such as those associated with scars, fibrosis, or radiation dermatitis; (13) vasculitis ulcerations, such as those associated with lupus erythematosus, rheumatoid arthritis, scleroderma, immune complex disease, pyoderma gangrenosum, or ulceration associated with lipodermatosclerosis; (14) infectious ulcerations, such as: (a) viral ulcerations, e.g. those associated with *Herpes simplex* or *Herpes zoster* in an immunocompromised or normal individual; (b) bacterial infections with ulcerations, such as those associated with tuberculosis, leprosy, swimming pool granuloma, ulceration over osteomyelitis, Buruli ulcer, gas gangrene, Meleny's ulcer, bacterial gangrene associated with other bacterial infection (e.g., streptococcal infection), scalded skin syndrome, ecthyma gangrenosum (such as can occur in children infected with *Pseudomonas aeruginosa*), and toxic epidermal necrolysis; (c) mycotic ulcerations, such as those associated with superficial fungal infection or deep fungal infection; (d) spirochetal ulcerations, such as those associated with syphilis or yaws: (e) leishmaniasis; (f) mydriasis; or (g) cellulitis; (15) surgical ulcerations, such as those associated with closed incisions or excisions, open incisions or excisions, stab wounds, necrotic incisions or excisions, skin grafts, or donor sites; or (16) other ulcerations, such as those associated with skin tears (traumatic ulcerations), fistula, peristomal ulcerations, ulcerations associated with aplasia cutis congenita, ulcerations associated with epidermolysis bullosa, ulcerations associated with ectodermal dysplasias, ulcerations associated with congenital protein C or S deficiency, ulcerations associated with congenital erosive and vesicular dermatosis, ulcerations associated with acrodermatitis enteropathica, and amputation stump ulcerations.

The peptides of the present invention can also be used to promote wound healing in other conditions.

VI. Pharmaceutical Compositions

Another aspect of the present invention is pharmaceutical compositions that include peptides according to the present invention. In general, a pharmaceutical composition of the present invention comprises: (1) a peptide according to the present invention in a physiologically effective quantity; and (2) a pharmaceutically acceptable carrier.

The physiologically effective quantity can be determined by one of ordinary skill in the art with reference to the dosages described above.

Conventional pharmaceutically acceptable carriers known in the art can include alcohols, e.g., ethyl alcohol, serum proteins, cholesterol, human serum albumin, liposomes, buffers such as phosphates, water, sterile saline or other salts, electrolytes, glycerol, hydroxymethylcellulose, propylene glycol, polyethylene glycol, polyoxyethylenesorbitan, other surface active agents, vegetable oils, and conventional anti-bacterial or anti-fungal agents, such as parabens, chlorobutanol, phenol, sorbic acid, thimerosal, and the like. A pharmaceutically-acceptable carrier within the scope of the present invention meets industry standards for sterility, isotonicity, stability, and non-pyrogenicity.

A preferred pharmaceutically acceptable carrier comprises Seamollient, water, a polymer selected from the group consisting of carboxymethylcellulose and hydroxyethylcellulose, and at least one preservative selected from the group consisting of methylparaben and propylparaben. Preferably, the pharmaceutically acceptable carrier comprises both methylparaben and propylparaben. A particularly preferred carrier has 78.5% by weight of water, 20% by weight of Seamollient, 0.5% by weight of methylparaben, 0.5% by weight of propylparaben, and 0.1% by weight of carboxymethylcellulose. Seamollient is available from Philip Rockley, Ltd. (East Setauket, N.J.) and is an extract of Hawaiian sea plants that acts as an emollient and moisturizer. It contains chlorphenesin, phenoxyethanol, propylene glycol, and sodium dehydroacetate as preservatives. Another particularly preferred carrier has 78.5% by weight of water, 20% by weight of Seamollient, 0.5% by weight of hydroxyethylcellulose, 0.5% by weight of methylparaben, and 0.5% by weight of propylparaben, Other carriers can be used and are known in the art.

The invention is illustrated by the following Examples. These Examples are for illustrative purposes only and are not intended to limit the invention.

EXAMPLES

Example 1

Effects of $TB_4$ and $TA_1$ on Endothelial Cell Migration

The effects of $TB_4$ and $TA_1$ on endothelial cell migration were determined. To investigate the possibility that these peptides effect the migration of normal human vascular endothelial cells (NHVEC) in vitro, a Boyden chamber migration assay was performed.

The results of these are shown in Table 1 and in FIG. 1. In the experiments of Table 1 and FIG. 1, normal human microvesicular endothelial cells are used at $5 \times 10^4$ cells per well. The wells are coated with 100 $\mu$g/ml bovine serum albumin Type IV.

These results demonstrate that both $TB_4$ and $TA_1$ act as chemoattractants for endothelial cells, stimulating the migration of NHVECs in Boyden chambers. At concentrations of 100 ng/ml, both $TB_4$ and $TA_1$ significantly enhanced cell migration over migration in the presence of media alone. Notably, $TB_4$ and $TA_1$ also revealed heightened responses at this concentration when compared to three positive controls:

vascular endothelial growth factor (VEGF), platelet derived growth factor (PDGF), and fibroblast growth factor (FGF). In addition, endothelial cell migration revealed a dose response to both peptides, as both $TB_4$ and $TA_1$ reached a maximal effect on migration at concentrations of 100 ng/ml.

TABLE 1

EFFECT OF PEPTIDES $TB_4$ AND $TA_1$ ON CELL MIGRATION

| Treatment | Concentration | Cell Number per HPF | | | | |
|---|---|---|---|---|---|---|
| | | Chamber 1 | Chamber 2 | Chamber 3 | Mean | SD |
| Blank | Medium only | 0 | 0 | 0 | 0 | 0 |
| Negative Control | Medium only | 12 | 30 | 13 | 18 | 10 |
| Positive Control | VEGF 10 ng/ml | 88 | 95 | 97 | 93 | 5 |
| $TB_4$ | 10 µg/ml | 70 | 77 | 66 | 71 | 6 |
| $TB_4$ | 5 µg/ml | 55 | 65 | 57 | 59 | 5 |
| $TB_4$ | 1 µg/ml | 45 | 47 | 63 | 52 | 10 |
| $TB_4$ | 0.5 µg/ml | 33 | 39 | 50 | 41 | 9 |
| $TB_4$ | 0.1 µg/ml | 18 | 12 | 26 | 19 | 7 |
| $TA_1$ | 10 µg/ml | 51 | 55 | 66 | 57 | 8 |
| $TA_1$ | 5 µg/ml | 35 | 64 | 72 | 57 | 19 |
| $TA_1$ | 1 µg/ml | 64 | 69 | 43 | 59 | 14 |
| $TA_1$ | 0.5 µg/ml | 52 | 53 | 57 | 54 | 3 |
| $TA_1$ | 0.1 µg/ml | 38 | 45 | 33 | 39 | 6 |

Example 2

Effects of $TB_4$ and $TA_1$ on Endothelial Cell Proliferation

Figure 2:
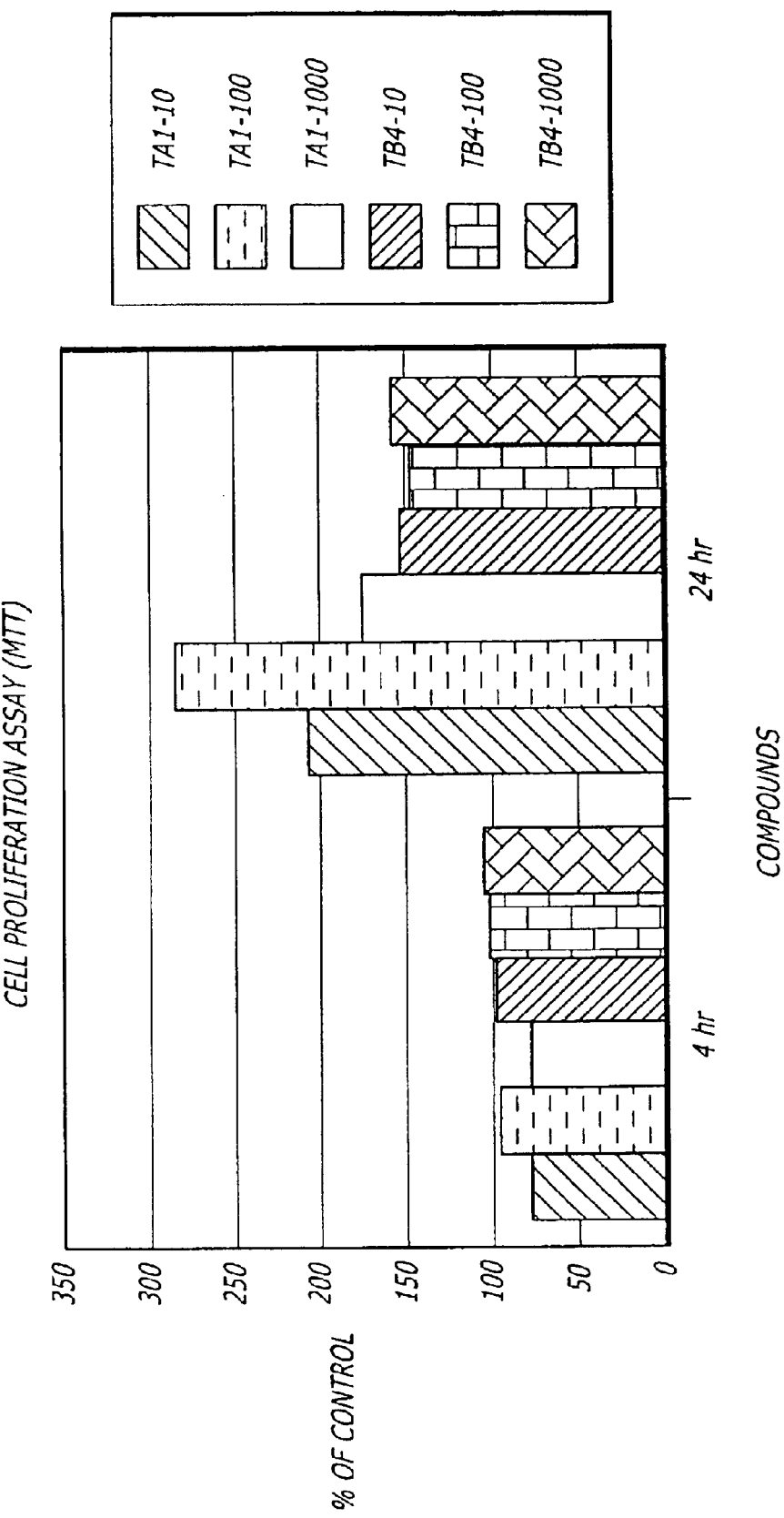
FIG. 2 is a graph showing the effects of the peptides $TB_4$ and $TA_1$ on proliferation of endothelial cells at 4 hours and 24 hours after stimulation as measured in a MTT (tetrazolium) assay.

The effects of $TB_4$ and $TA_1$ on endothelial cell proliferation were determined using a MTT (tetrazolium) assay. The results are shown in FIG. 2 for 4 hours and 24 hours and for three concentrations of these peptides, 10 ng/ml, 100 ng/ml, and 1000 ng/ml. These results show that these peptides stimulate endothelial cell proliferation. At a concentration of 10 ng/ml, $TB_4$ and $TA_1$ maximally stimulated cell proliferation approximately 2-fold and 3-fold over that of the control, respectively.

Example 3

Effects of $TB_4$ and $TA_1$ on Endothelial Cell Proliferation

To examine the effects of $TB_4$ and $TA_1$ (10 ng/ml) on NHVEC migration, a scratch would closure assay was used. When a confluent monolayer was scratched, migration of cells into the wounded area was significantly increased in the presence of $TB_4$ and $TA_1$ compared to migration with media alone.

Thus, these peptides significantly enhance endothelial cell migration, proliferation, and angiogenesis, and may play an important role in the wound healing process.

Example 4

Clinical Effects of $TB_4$ $TB_4$ used in vivo revealed several clinical effects. One was the effect on reducing the erythema of the healed wound (e.g., on the shin). There was not post-inflammatory erythema and hyperpigmentation. Frequently, the skin color was normal and not the expected deep red-purple with brown coloration that would take months to resolve on the leg. The wounds in other areas also did not leave residual erythema or hyperpigmentation that is typically seen in wound healing. To extend this concept, $TB_4$ was tested on poikiloderma vasculare of the neck secondary to chronic sun exposure, with indications that the erythema was reducing, although not enough of the peptide was available to continue the evaluation.

Another effect seen is the reduction of melanin pigmentation on the areas of treatment with $TB_4$. There is a definite reduction in the clinical intensity of brown melasma, lentigines, post-inflammatory hyperpigmentation and ephelides after treatment with the $TB_4$ peptide.

Example 5

Pharmaceutical Composition According to the Present Invention

A pharmaceutical composition according to the present invention comprises 78.49999 g of water, 20 g of Seamollient; 0.5 g of hydroxyethylcellulose, 0.5 g of methylparaben, 0.5 g of propylparaben, and 10 µg of the active peptide.

Example 6

Clinical Course of Patients Undergoing Treatment with Peptides according to the Present Invention Patient 1 (A.T.)

Figure 3:
FIG. 3 is a photograph of an ulcer on the shin of a first patient (A.T.) before treatment.

A.T. was seen with a history of an injury on the left lower anterior leg (shin) which had occurred approximately five months previously. The injury started with a bruise on the left shin, but approximately seven weeks later the area started to get erythematous. The patient was sent by the general internist to the local hospital wound healing center, where the wound was debrided and Silvadene cream was used. However, the patient was not progressing well and grafting was considered. The patient did not want to undergo surgery. The underlying problem was venous stasis with the development of ulceration secondary to minor trauma. The ulcer was about 3.0 cm by 1.0 cm in size with a 1-cm rim of mild erythema. There was a small superior 4 mm deeper area of the ulcer. The wound at this stage is shown in FIG. 3. The patient was given a preparation containing $TA_1$ to be used twice daily to the small 4 mm area.

Figure 4:
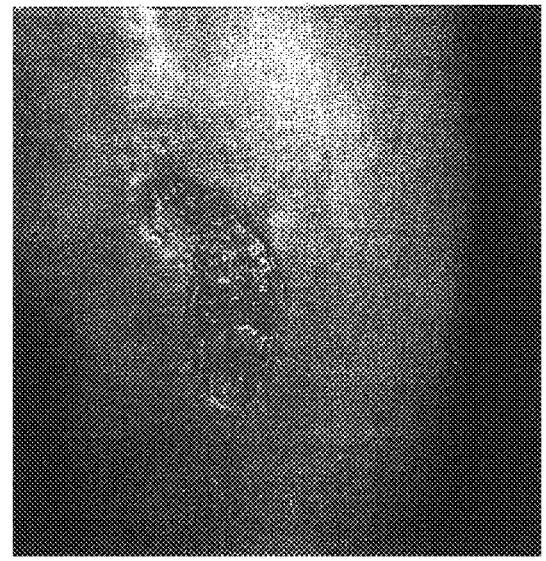
FIG. 4 is a photograph of the ulcer on the shin of A.T. after one week of treatment with $TA_1$, showing improvement.

After 1 week, improvement was noted as shown in FIG. 4. The treatment with $TA_1$ was continued for another week twice daily.

Figure 5:
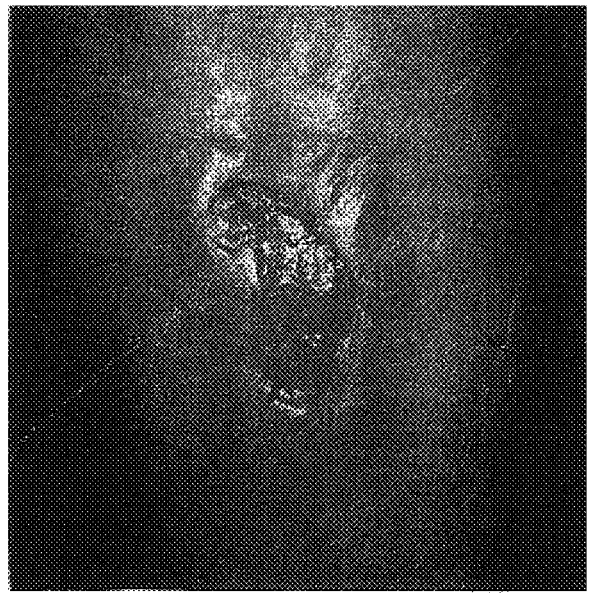
FIG. 5 is a photograph of the ulcer after an additional week of treatment.

After another week, the deeper 4 mm area of the ulceration was now level with the rest of the ulcer as shown in FIG. 5. At this point, treatment was changed to a preparation containing $TB_4$ to be applied twice daily to the entire ulcer.

Figure 6:
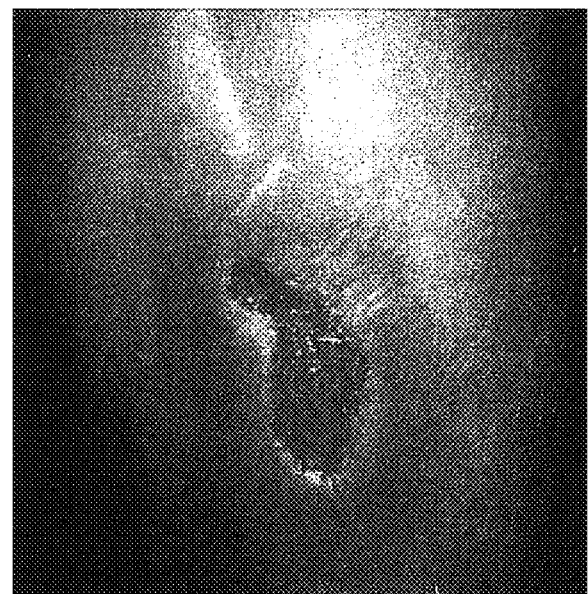
FIG. 6 is a photograph of the ulcer after further treatment with $TB_4$.

After the entire ulcer had been treated for seven days with $TB_4$ twice daily, it was noted that the size of the ulcer was starting to reduce. It was now 2.3 cm×0.8 cm with more reepithelialization and slightly more erythema surrounding the ulcer as shown in FIG. 6. The wound center physician was concerned about infection (cellulitis around the ulcer). The patient was placed on oral antibiotics for 10 days. However, when the surrounding erythema was palpated, there was no tenderness. The wound appeared to be repairing and increasing the vascular flow to the ulcer base and surrounding skin. The patient felt that after treating the entire for seven days she improved by 40%. The patient was given more preparation containing $TB_4$ for the next week. The internist felt that the patient should not undergo surgery for grafting due to cardiac problems in view of the improvement in the wound.

After another seven days, the status of the ulcer was as shown in FIG. 7. The ulcer continued to reepithelialize from the bottom of the ulcer. The depth of the ulcer was very shallow. Although the size of the ulcer was the same, there were peripheral islands of healing occurring making the entire ulcer smaller. The patient had not taken any antibiotics. At this point, the administration of $TB_4$ was temporarily suspended and the patient used Silvadene cream and Vigilon.

After another seven days, the status of the ulcer was as shown in FIG. 8. After the patient had used Silvadene and Vigilon, the ulcer continued to improve. The administration of $TB_4$ was restarted and Silvadene was stopped.

After another eight days, the status of the ulcer was as shown in FIG. 9. The ulcer had reduced to 2.0 cm×0.5 cm with the upper pole almost closed. The patient was still using the Vigilon which may have absorbed the $TB_4$ preparation. The patient was told to stop the Vigilon and continue twice daily with the $TB_4$ preparation.

After another six days, the status of the ulcer was as shown in FIG. 10. The ulcer was closing in and was 1.9 cm×0.4 cm. The upper pole had just a 2–3 mm zone to close.

Figure 11:
FIG. 11 is a photograph of the ulcer after nine days of additional treatment.

After another nine days, the status of the ulcer was as shown in FIG. 11. The ulcer was reducing very well. The ulcer size was now 0.8 cm×0.3 cm with the $TB_4$ preparation continued.

After another seven days, the ulcer had almost completely closed with a dry scab formation occurring. The $TB_4$ preparation was continued, once daily, treating the scabbed area.

Figure 12:
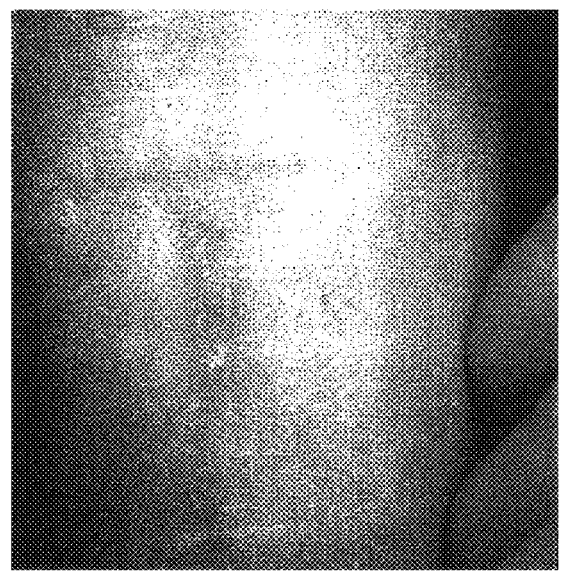
FIG. 12 is a photograph of the ulcer after an additional three weeks, showing additional improvement.

After another two weeks, the amount of scab had reduced with no ulceration, as shown in FIG. 12. The $TB_4$ preparation was continued once daily to the scab.

In summary, considerable improvement was shown with administration of peptides according to the present invention in this venous stasis ulceration. Once the wound healing preparation stimulated reepithelialization there seemed to be some continuation of the wound repair even during the week the patient was not using the peptide. The erythema surrounding the ulcer may related to the repair process in the initial stages. The erythema reduced and disappeared once the major portion of wound repair occurred.

Patient 2 (P.M.)

The patient had a history of diabetes mellitus for greater than 10 years and had developed ulcerations of her fingers secondary to burns since she developed diabetic neuropathy and lost sensation in her fingers. The glucose levels of the patient were not kept under control. The patient developed heat burns with blistering and erosions on the patient's fingers. The ulcers are cleansed and Silvadene cream is used for wound healing, which usually takes 2–4 weeks. Occasionally, systematic antibiotics are given.

Figure 13:
FIG. 13 is a photograph of an ulcer on the finger of a second patient (P.M.) with diabetes mellitus before treatment.

The patient was seen after having burned the distal phalanx of the left middle finger with a hairdryer 10 days before. The patient had taken some leftover Ceftin 250 mg twice daily and has used Silvadene cream twice daily for the 10 days, but the ulcer would not heal. The status of the ulcer at this time was as shown in FIG. 13. The ulcer was debrided and the patient was given a preparation containing $TA_5$ to use on the ulcer base twice daily. This ulcer was on the lateral thenar side of the left middle finger.

Figure 14:
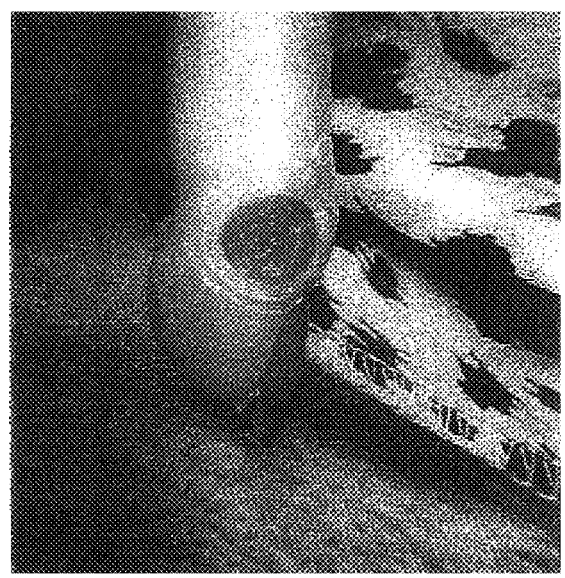
FIG. 14 is a photograph of the ulcer after one week of treatment with $TA_5$, showing considerable improvement.

One week later the status of the ulcer was as shown in FIG. 14. There was a dramatic improvement of the ulcer base. Reepithelialization was occurring well at the base of the ulcer. The patient had developed another ulceration on the same finger, left middle finger, on the palmar side two days prior to the visit. The patient was requested to use the preparation containing $TA_5$ to both ulcerations.

One week later after using the preparation containing $TA_5$ twice daily to the new shallow ulceration there was marked improvement, with the ulcer being approximately 70% resolved. The older, deeper ulceration was also healing more rapidly than previously.

Figure 15A:
FIG. 15(a) is a photograph of a new ulceration that subsequently developed on the finger of P.M.
Figure 15B:
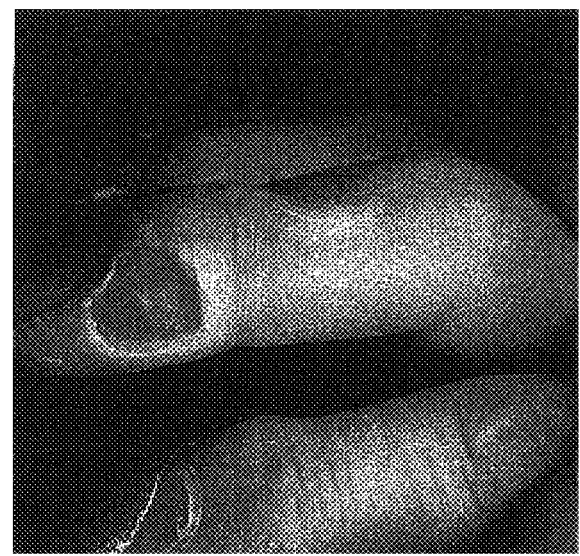
FIG. 15(b) is a photograph of a second ulceration that subsequently developed on the finger of P.M.

Approximately six weeks later, the patient had developed new ulcerations of the right index finger on the palmar-ventral side (5 days), and two ulcerations on the right middle finger on the distal digit, lateral thenar side (5 days) and the second digit on the dorsal side (2 weeks history). These ulcerations had developed after the patient had handled hot items. These ulcerations are shown in FIG. 15(a) and FIG. 15(b). Dicloxacillin (500 mg twice daily) was given for 10 days. The patient was given $TB_4$ wound healing preparation to be used twice daily to the ulcerations.

Figure 16:
FIG. 16 is a photograph of the ulcerations after one week of treatment with $TB_4$, showing considerable improvement.

After another week, the patient had experienced considerable (70–80% improvement) in the ulcerations after using $TB_4$ wound healing preparation. This is shown in FIG. 16.

Figure 17:
FIG. 17 is a photograph of the ulcerations after another five days of treatment with $TB_4$, showing considerable further improvement.

After another five days, the ulcers were approximately 90% cleared as shown in FIG. 17, despite the fact that the patient's diabetes was still out of control.

Example 7

Effect of $TA_1$ on Wound Healing in vivo

To study the effect of $TA_1$ on wound healing in vivo, full thickness punch wounds were made in rat skin and treated with $TA_1$ topically or by intraperitoneal injection with a seven-day study interval. For topical treatment, 5 $\mu$g of $TA_1$ was applied in 50 $\mu$l saline on injury date and 48 hours post-injury. For intraperitoneal treatment, 60 $\mu$g of $TA_1$ was administered in 300 $\mu$l saline on injury date and then every other day.

Figure 18:
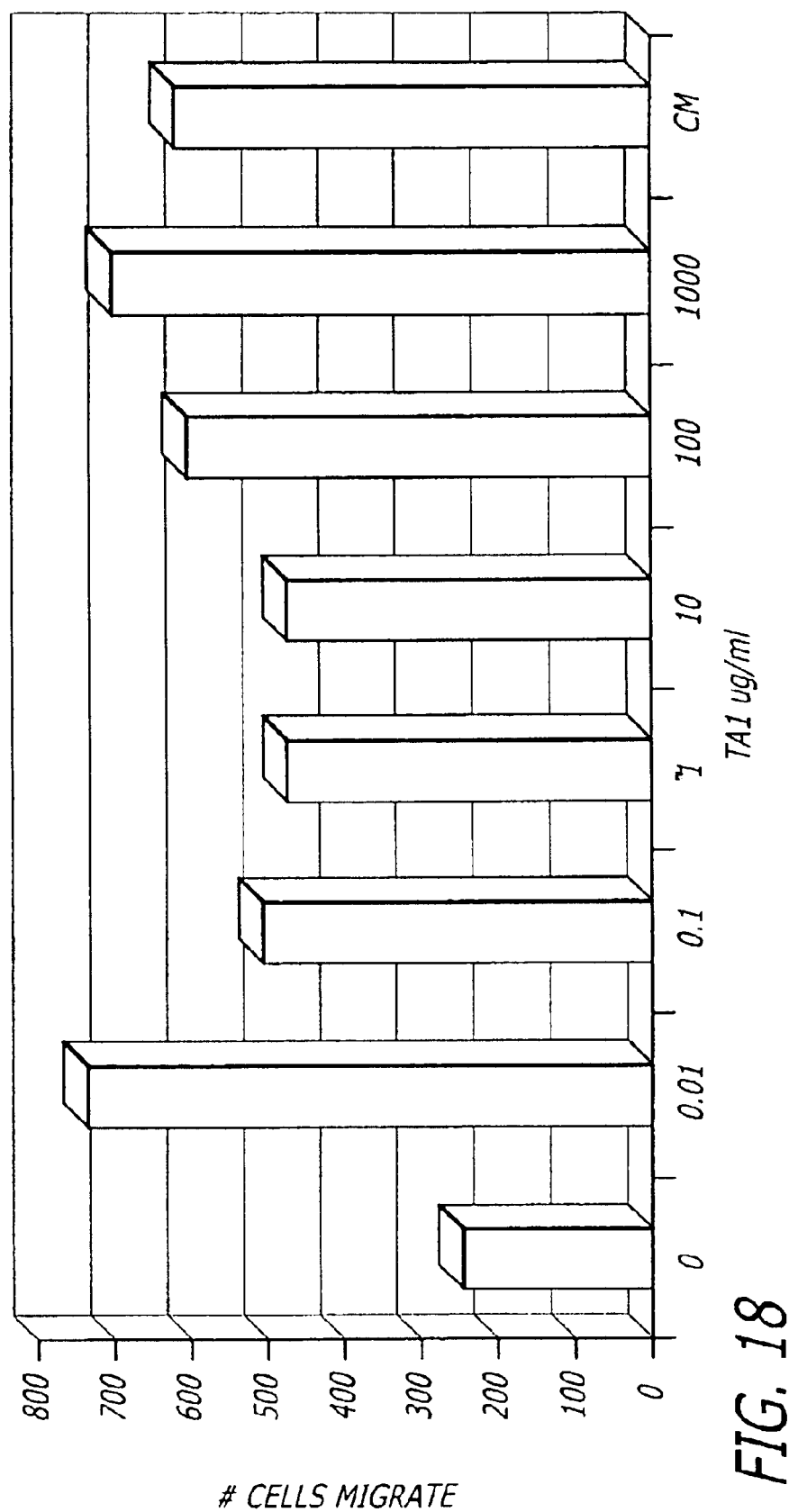
FIG. 18 is a graph showing the effect of varying concentrations of $TA_1$ on keratinocyte migration as measured in the Boyden chamber in an in vivo experiment in rats.

The effect of varying concentrations of $TA_1$ on keratinocyte migration as measured in the Boyden chamber is shown in FIG. 18.

Figure 19:
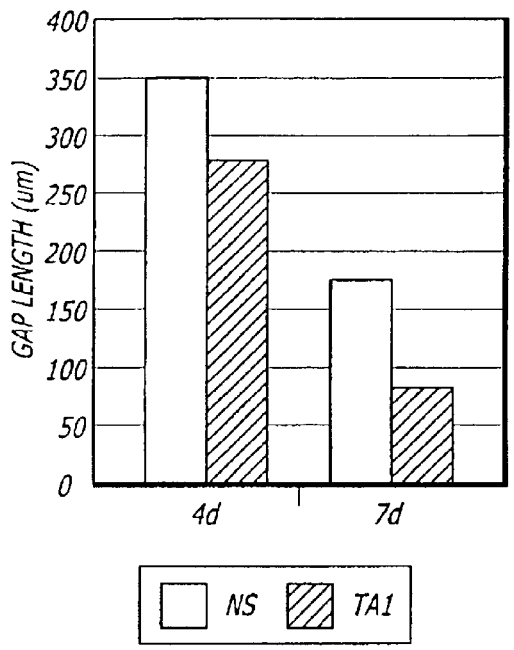
FIG. 19 is a graph showing the effect of the topical $TA_1$ and normal saline (NS) on gap closure in the wounds in vivo for 4 and 7 days post-injury.
Figure 20:
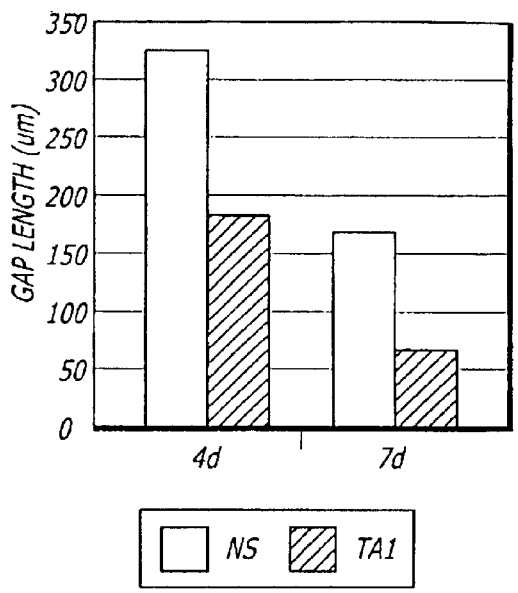
FIG. 20 is a graph showing the effect of the intraperitoneal $TA_1$ and normal saline (NS) on gap closure in the wounds in vivo for 4 and 7 days post-injury.

The effect of the topical $TA_1$ on gap closure in the wounds in vivo is shown in FIG. 19 for 4 and 7 days post-injury. There was an 18%±12% decrease in gap size versus a normal saline (NS) control, which is significant for the seven-day results (p 0.04). For intraperitoneal administration as shown in FIG. 20 for 4 and 7 days post-injury, there was a 42%±9% decrease in gap size versus a normal saline (NS) control, which was highly significant (p 0.0007) for both the four-day and seven-day results.

Figure 21:
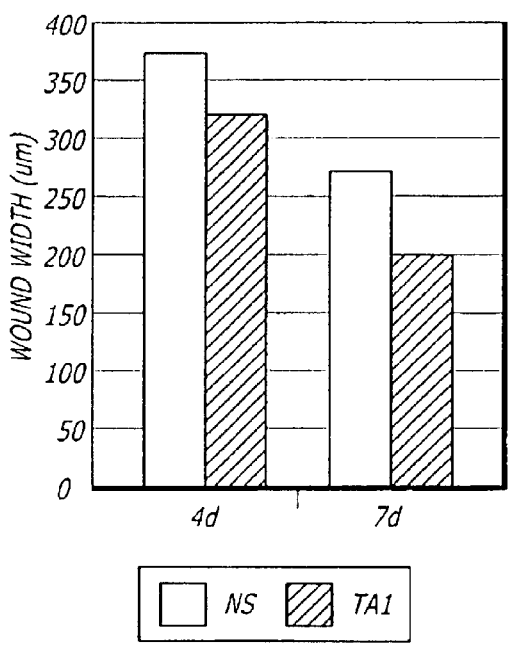
FIG. 21 is a graph showing the effect of the topical $TA_1$ and normal saline (NS) on wound width in the wounds in vivo for 4 and 7 days post-injury.
Figure 22:
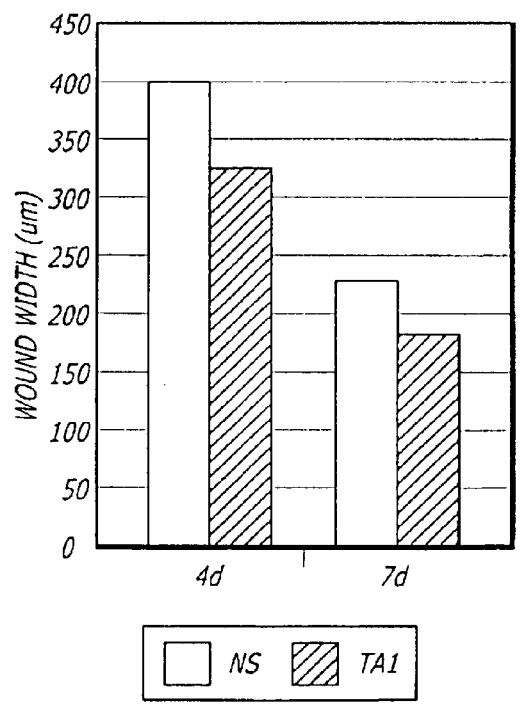
FIG. 22 is a graph showing the effect of the intraperitoneal $TA_1$ and normal saline (NS) on wound width in the wounds in vivo for 4 and 7 days post-injury.

The effect of the topical $TA_1$ on wound width in the wounds in vivo is shown in FIG. 21 for 4 and 7 days post-injury. There was a 15% decrease in wound width versus a normal saline (NS) control, which is highly significant for the four and seven-day results. (p 0.0001). For intraperitoneal administration as shown in FIG. 22 for 4 and 7 days post-injury, there was a 42%±9% decrease in wound width versus a normal saline control, which was highly significant (p 0.0001) for the four-day and marginally significant (p 0.08) for the seven-day results.

Figure 23:
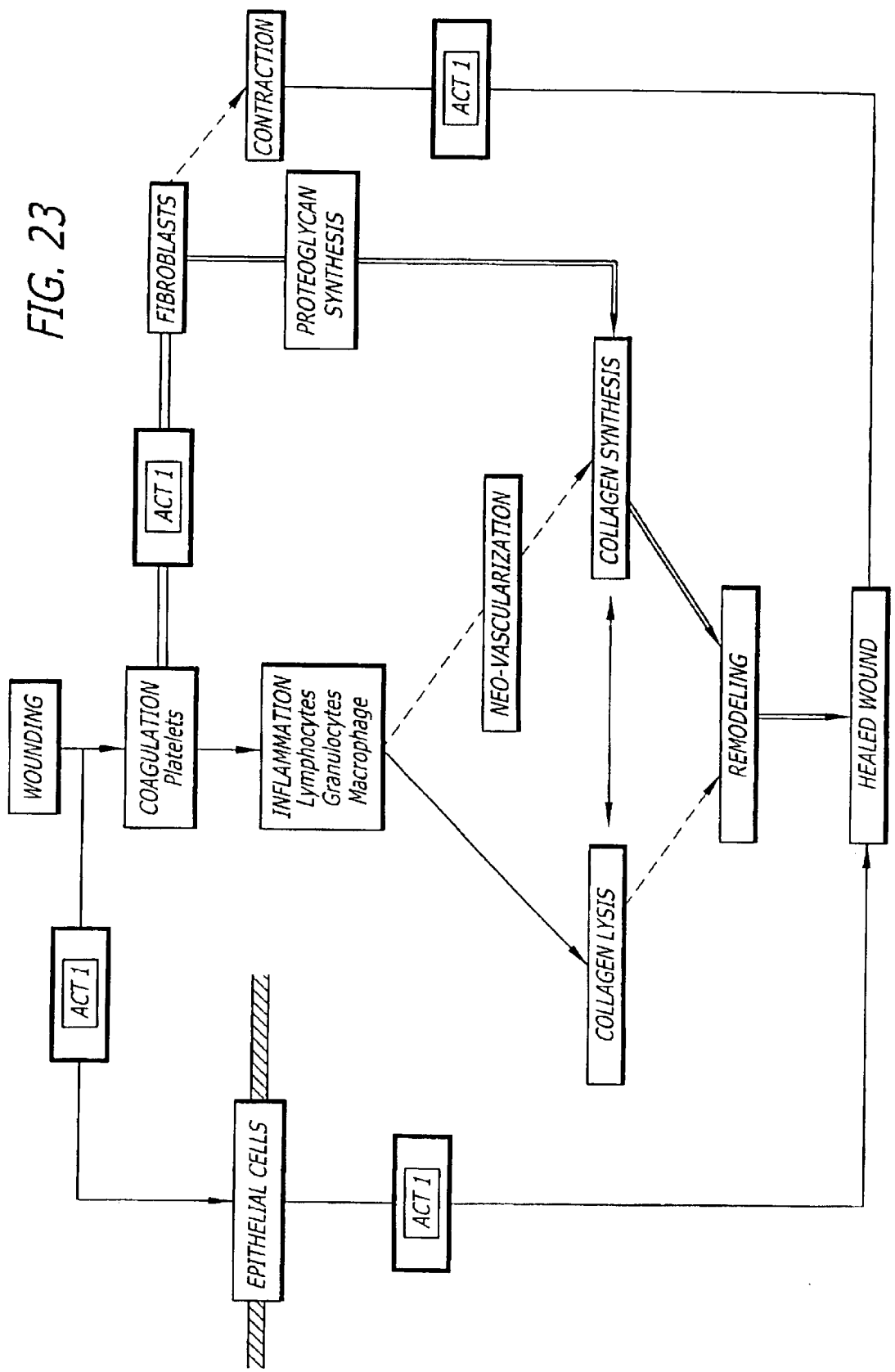
FIG. 23 is a chart showing a model of wound healing that depicts possible points of action of peptides according to the present invention.

In summary, the 4-day post-injury findings indicated accelerated reepithelialization, wound contraction, and keratinocyte migration, as well as increased capillary ingrowth and collagen deposition. Although Applicant does not intend to be bound by this model, a possible model of the actions of $TA_1$ is shown in FIG. 23. In this figure, "ACT 1" refers to the peptide $TA_1$.

Similar results were seen with $TA_5$. In conclusion, these peptides appear to interact with G-actin, mediate cell proliferation, migration, and differentiation, and stimulate angiogenesis. These peptides are also involved in differentiation of vascular endothelial cells and accelerate the migration of vascular endothelial cells into the scratch wounded area, the peptides also accelerate the production of matrix metalloproteinases that may degrade basement membranes during angiogenesis. They show efficacy with topical application and intraperitoneal injection. The potency of these intraperitoneal effects support high diffusibility in tissue.

Example 8

Figure 24:
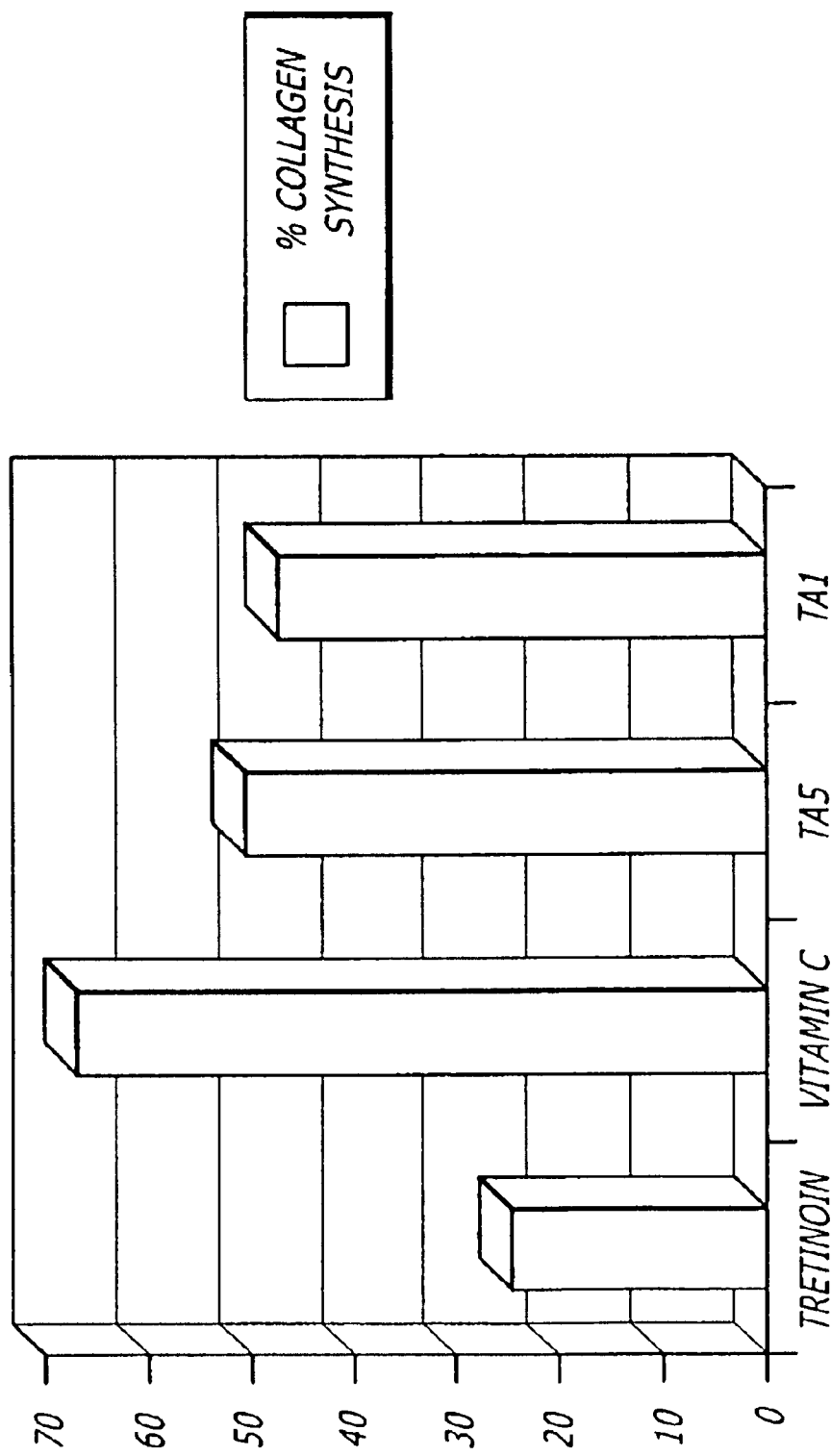
FIG. 24 is a graph showing the effect of peptides $TA_1$ and $TA_5$ on the stimulation of collagen synthesis in chronic wounds in humans as compared with tretinoin and vitamin C.

Pilot Study in Humans of $TA_1$ and $TA_5$ in Comparison to Vitamin C and Tretinoin A pilot study of $TA_1$ and $TA_5$ was performed in humans with 20 volunteers with chronic wounds. Skin biopsies were taken at the baseline and at two months, subjected to histological analysis, immunohistological analysis, and objective and subjective observation. Immunohistochemistry endpoints were epidermal differentiation, epidermal proliferation, and markers of inflammation and were assayed by using anti-CD3 monoclonal antibody. Preliminary results from this study in terms of collagen synthesis are shown in FIG. 24. These results indicate that the peptides $TA_1$ and $TA_5$ were more effective in stimulating collagen synthesis than tretinoin or vitamin C.

Advantages of the Invention

Although the present invention has been described in considerable detail, with reference to certain preferred versions thereof, other versions and embodiments are possible. Therefore, the scope of the invention is determined by the following claims.

I claim:

1. A substantially purified peptide having wound healing activity, the peptide comprising a sequence of 44 amino acids, that is: K-K-L-K-K-E-E-N-P-L-E-L-K-E-K-L-K-E-K-K-N-P-L-P-S -K-E-E-E-K-A-S-P-F-D-K-I-T-E-T-P-D-M-S (SEQ ID NO: 8), the peptide being linear.

2. A pharmaceutical composition comprising:
 (a) the peptide of claim 1 in a physiologically effective quantity; and
 (b) a pharmaceutically acceptable carrier.

3. The pharmaceutical composition of claim 2 wherein the pharmaceutically acceptable carrier comprises an extract of Hawaiian sea plants that acts as an emollient and moisturizer and includes chlorphenesin, phenoxyethanol, propylene glycol, and sodium dehydroacetate as preservatives, water, a polymer selected from the group consisting of carboxymethylcellulose and hydroxyethylcellulose, and at least one preservative selected from the group consisting of methylparaben and propylparaben.

* * * * *